(12) United States Patent
Heinrich

(10) Patent No.: US 6,959,851 B2
(45) Date of Patent: Nov. 1, 2005

(54) SURGICAL STAPLING DEVICE WITH TISSUE TENSIONER

(75) Inventor: Russell Heinrich, Ltichfield, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 10/892,574

(22) Filed: Jul. 16, 2004

(65) Prior Publication Data

US 2005/0021053 A1 Jan. 27, 2005

Related U.S. Application Data

(60) Provisional application No. 60/487,841, filed on Jul. 16, 2003.

(51) Int. Cl.[7] ............................................. A61B 17/068
(52) U.S. Cl. ........................ 227/175.1; 227/19; 227/152
(58) Field of Search ................................ 227/19, 175.1, 227/176.1, 180.1, 152; 606/139, 219, 142, 153

(56) References Cited

U.S. PATENT DOCUMENTS

| | | |
|---|---|---|
| 3,388,847 A | 6/1968 | Kasulin et al. |
| 3,552,626 A | 1/1971 | Astafiev |
| 3,638,652 A | 2/1972 | Kelley |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |

(Continued)

FOREIGN PATENT DOCUMENTS

| | | |
|---|---|---|
| CA | 908529 | 8/1972 |
| CA | 1136020 | 1/1982 |
| DE | 1057729 | 5/1959 |
| DE | 1835500 | 4/1961 |
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| FR | 1461464 | 12/1966 |
| FR | 1588250 | 4/1970 |
| FR | 1136020 | 12/1979 |
| FR | 2443239 | 12/1979 |
| GB | 1185292 | 3/1970 |
| GB | 2016991 | 9/1979 |
| GB | 2070499 | 9/1981 |
| NL | 7711347 | 10/1977 |
| WO | 8706448 | 11/1987 |
| WO | 8900406 | 1/1989 |
| WO | 9006085 | 6/1990 |

*Primary Examiner*—Scott A. Smith

(57) ABSTRACT

A circular stapling device particularly suited for surgical treatment of internal hemorrhoids is provided. The stapling device includes a distal head portion having an anvil and a shell assembly. A tissue tensioner device including a tissue engagement member is movably positioned between the anvil and the shell assembly and is operable via a tensioner trigger to position tissue within a bore defined within the shell assembly.

18 Claims, 7 Drawing Sheets

U.S. PATENT DOCUMENTS

| | | |
|---|---|---|
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,754,909 A | 7/1988 | Barker et al. |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,285,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,326 A * | 4/1995 | Harrison et al. ............ 606/139 |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,470,006 A | 11/1995 | Rodak |
| 5,474,223 A | 12/1995 | Viola et al. |
| 5,497,934 A | 3/1996 | Brady et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,588 A * | 5/1997 | Sauer et al. ................ 606/144 |
| 5,632,433 A | 5/1997 | Grant et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A | 11/1997 | Seeber |
| 5,697,943 A * | 12/1997 | Sauer et al. ................ 606/153 |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,758,814 A | 6/1998 | Gallagher et al. |
| 5,799,857 A | 9/1998 | Robertson et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,964,782 A * | 10/1999 | Lafontaine et al. .......... 606/213 |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,113,609 A * | 9/2000 | Adams ....................... 606/139 |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,494,888 B1 * | 12/2002 | Laufer et al. ................ 606/153 |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,595,887 B2 | 7/2003 | Thoma |

| | | | | | | |
|---|---|---|---|---|---|---|
| 6,601,749 B2 | 8/2003 | Sullivan et al. | | 6,685,079 B2 | 2/2004 | Sharma et al. |
| 6,605,078 B2 | 8/2003 | Adams | | 6,695,198 B2 | 2/2004 | Adams et al. |
| 6,623,227 B2 | 9/2003 | Scott et al. | | 6,695,199 B2 | 2/2004 | Whitman |
| 6,626,921 B2 | 9/2003 | Blatter et al. | | 6,716,222 B2 | 4/2004 | McAlister et al. |
| 6,629,630 B2 | 10/2003 | Adams | | 6,716,233 B1 | 4/2004 | Whitman |
| 6,631,837 B1 | 10/2003 | Heck | | 6,742,692 B2 | 6/2004 | Hartwick |
| 6,632,227 B2 | 10/2003 | Adams | | 6,763,993 B2 | 7/2004 | Bolduc et al. |
| 6,632,237 B2 | 10/2003 | Ben-David et al. | | 6,769,590 B2 | 8/2004 | Vresh et al. |
| 6,659,327 B2 | 12/2003 | Heck et al. | | 6,773,440 B2 * | 8/2004 | Gannoe et al. ............ 606/142 |
| 6,676,671 B2 | 1/2004 | Robertson et al. | | | | |
| 6,681,979 B2 | 1/2004 | Whitman | | * cited by examiner | | |

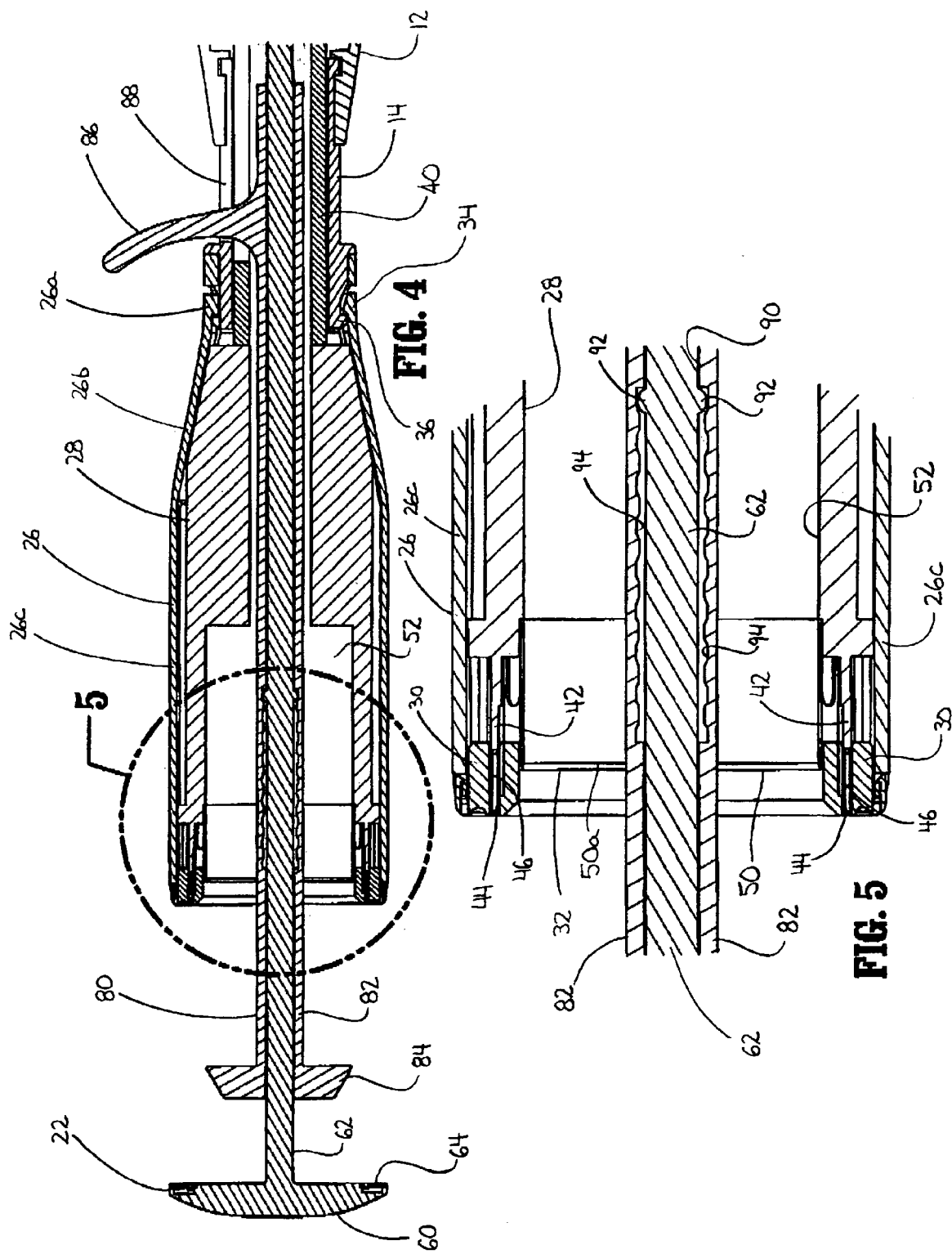

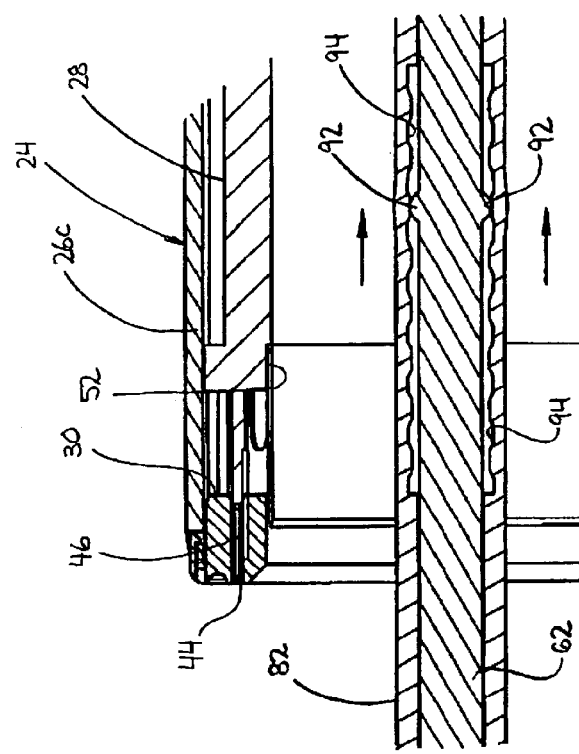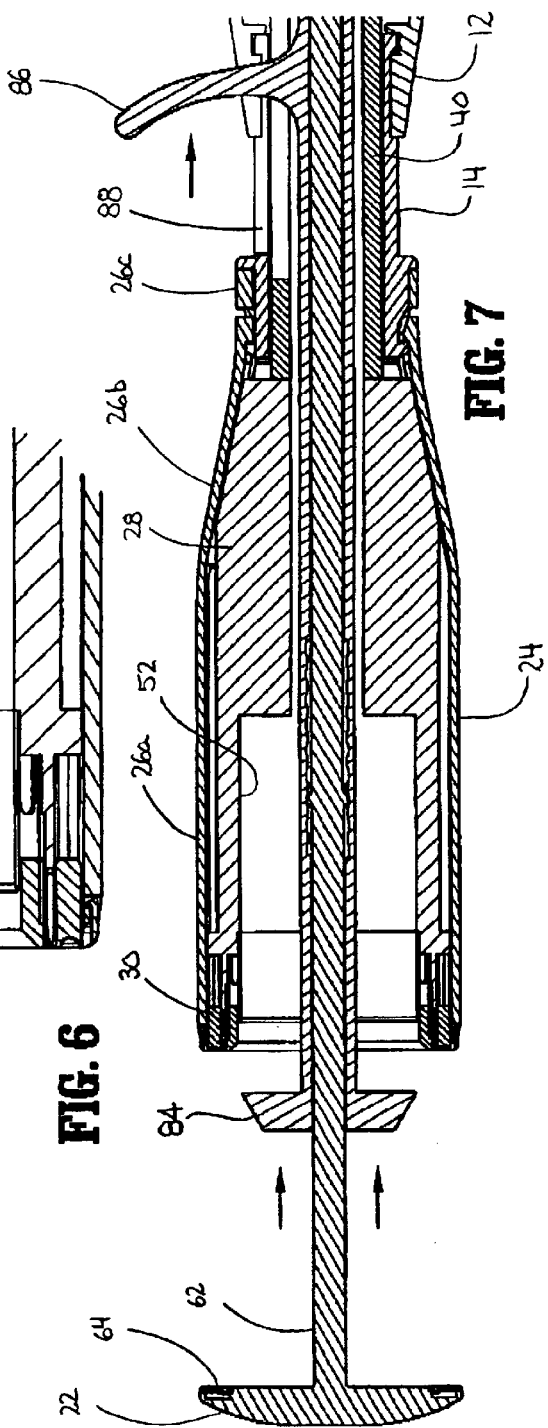

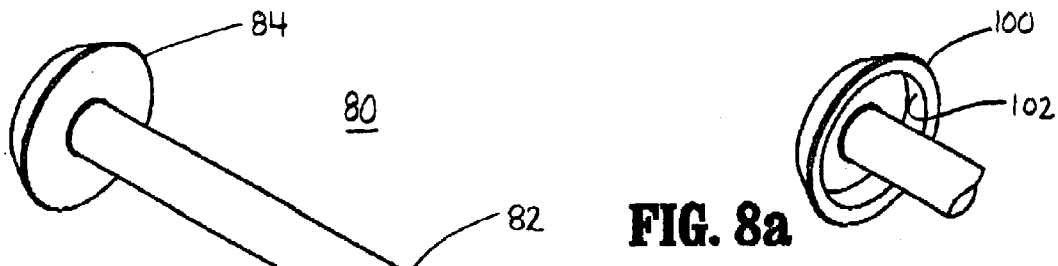
FIG. 8a
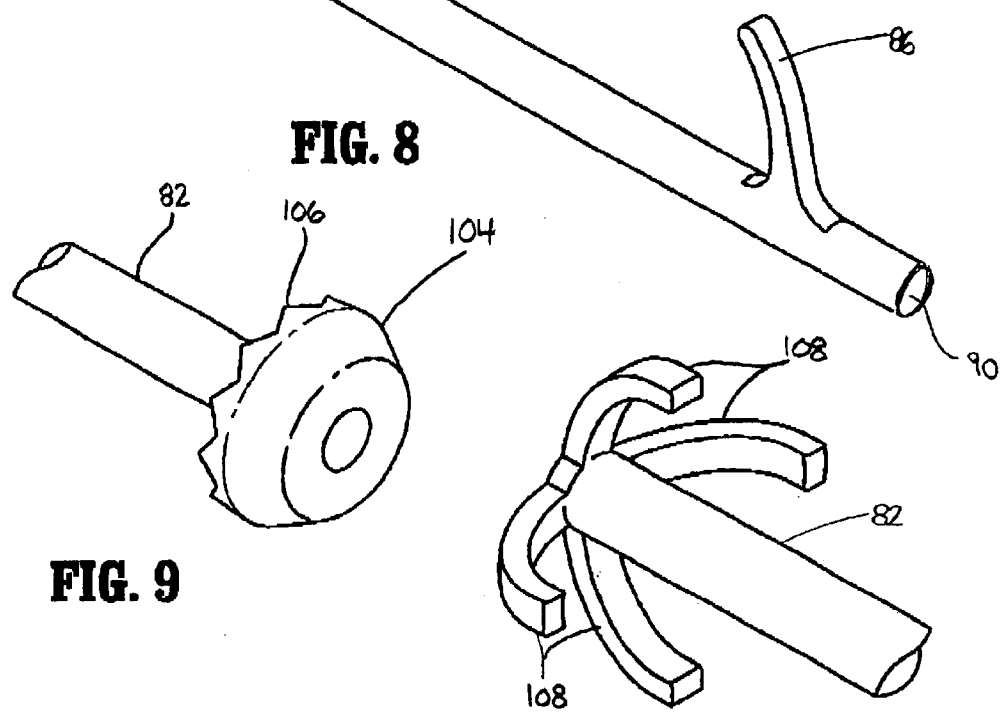
FIG. 8
FIG. 9
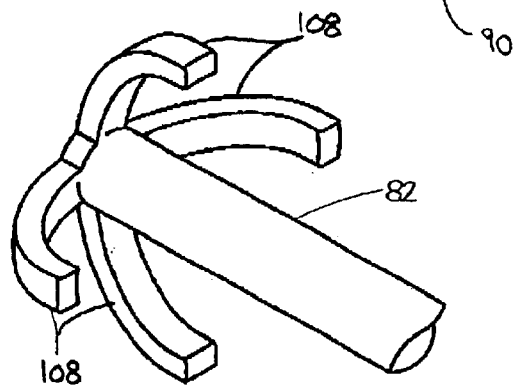
FIG. 10
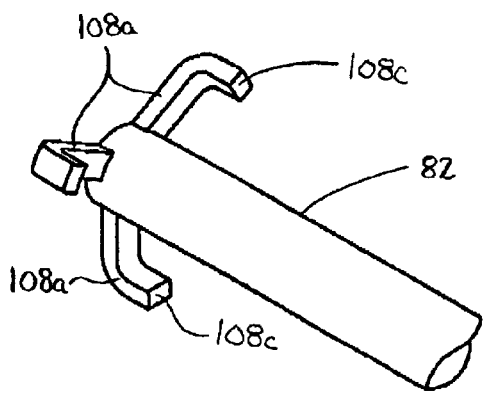
FIG. 11

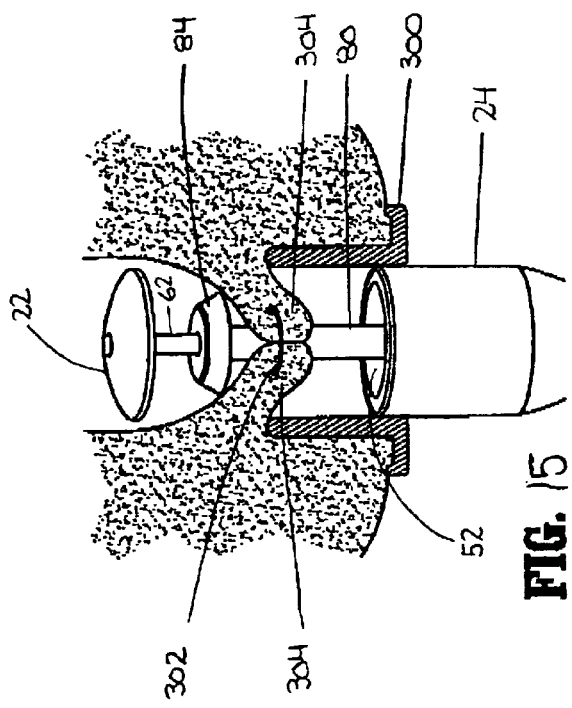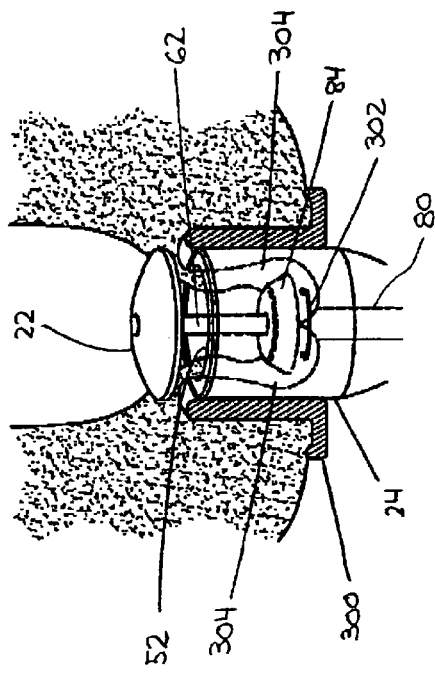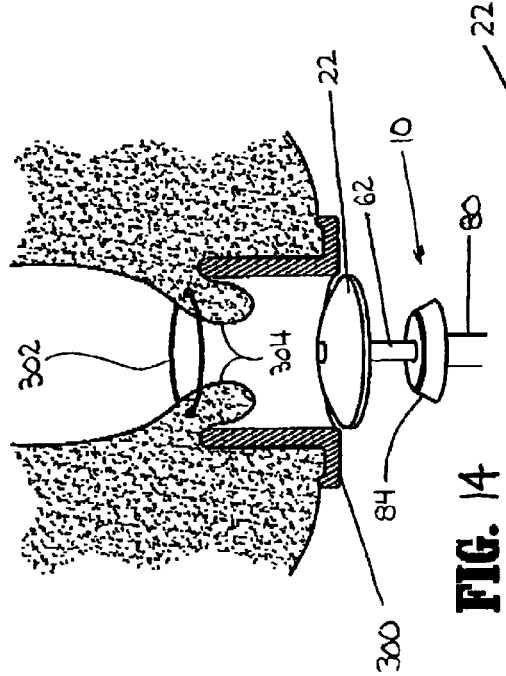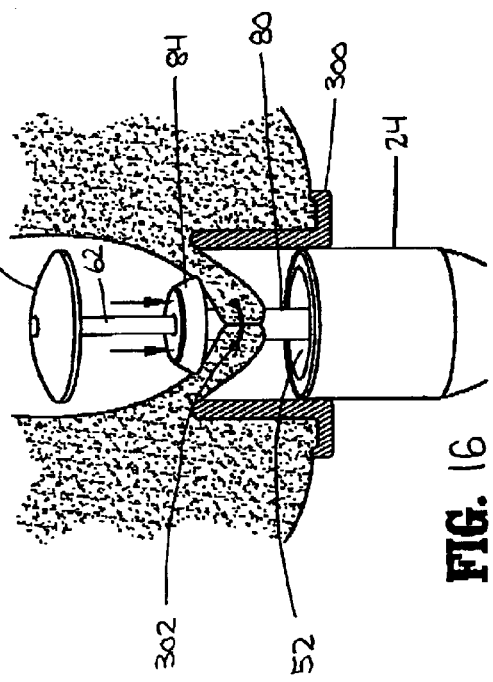

SURGICAL STAPLING DEVICE WITH TISSUE TENSIONER

This application claims priority from U.S. provisional application Ser. No. 60/487,841 filed Jul. 16, 2003, the entire contents of which are incorporated herein by reference.

BACKGROUND

1. Technical Field

The present disclosure relates generally to a surgical device for treating hollow tissue organs. More particularly, the present disclosure relates to a surgical stapling device suitable for the treatment of internal hemorrhoids.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a known circular anastomosis procedure, two ends of organ sections are joined by means of a stapling device which drives a circular array of staples through the end of each organ section and simultaneously cores any tissue interior of the driven circular array of staples to free a tubular passage. Examples of devices for performing circular anastomsis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these devices include an elongated shaft having a handle portion at a proximal end thereof to effect actuation of the device and a staple holding component disposed at a distal end thereof. An anvil assembly including an anvil rod with attached anvil head is mounted to the distal end of the device adjacent a staple holding component. Opposed end portions of tissue of the hollow organ(s) to be stapled are clamped between the anvil head and the staple holding component of the device. The clamped tissue is stapled by driving one or more staples from the staple holding component so that the ends of the staples pass through the tissue and are deformed by the anvil head. An annular knife is concurrently advanced to core tissue within the hollow organ to free a tubular passage within the organ.

Surgical stapling devices for performing circular anastomosis have also been used to treat internal hemorrhoids in the rectum. During the use of a circular stapling device for hemorrhoid treatment, the anvil head and the staple holding component of the surgical stapling device are inserted through the anus and into the rectum with the anvil head and the staple holding component in an open or unapproximated position. Thereafter, a pursestring suture is used to pull the internal hemorrhoidal tissue and/or mucosal tissue towards the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut tissue.

Although the use of circular anastomosis staplers for hemorrhoid treatment has many benefits, some problems do exist. For example, during approximation of the anvil head and staple holding component of the surgical stapling device, it is sometimes difficult to properly position tissue to be removed within the staple holding component of the surgical stapling device. As such, the tissue may bunch up in a tissue gap defined between the anvil head and the staple holding component of the instrument. This may result in malformed staples and/or ineffective removal of all the desired tissue.

Accordingly, a continuing need exists in the art for a circular stapling device for the treatment of tissue which can quickly and easily position tissue to be removed within the staple holding component of the surgical stapling device.

SUMMARY

In accordance with the present disclosure, a circular stapling device having a tissue tensioner is disclosed. The stapling device includes a proximal handle portion, a central body portion, and a distal head portion. The distal head portion has an anvil and a shell assembly defining an internal bore or chamber. The anvil includes an anvil head and an anvil shaft. The anvil is movable in relation to the shell assembly from an unapproximated position, wherein the anvil head is spaced from the shell assembly, to an approximated position, wherein the anvil head is in close juxtaposed alignment with the shell assembly. A tissue tensioning device is supported on the anvil shaft and is movable in relation to the anvil and in relation to the shell assembly between advanced and retracted positions. When the anvil is in its approximated position, a tissue engagement member of the tissue tensioning device is positioned at least partially within the bore of the shell assembly.

In one embodiment, the tissue tensioning device includes a hollow shaft and a trigger. The tissue engagement member extends radially outwardly from the hollow shaft. The hollow shaft is slidably positioned about the anvil shaft and is movable to shift the position of the tissue engagement member in relation to the anvil and the shell assembly. In another embodiment, the anvil shaft defines a longitudinal bore and the tissue tensioning device includes a tensioner shaft which is slidably positioned within the longitudinal bore of the anvil shaft. In each embodiment, the tissue tensioning device trigger extends through a slot formed in the surgical stapling device and can be manually manipulated by a surgeon to adjust the position of the tissue engagement member with respect to the anvil and the shell assembly.

In another embodiment, one of the anvil shaft and the tissue tensioner shaft includes a series of indentations and the other of the anvil shaft and tissue tensioner shaft includes a projection or nub which is releasably received in one of the indentations to releasably retain the tissue tensioner device at a fixed position in relation to the anvil shaft. A predetermined force can be applied to the tissue tensioner trigger to disengage the nub from a respective indentation to facilitate movement of the tissue tensioner device in relation to the anvil and the shell assembly.

In yet another embodiment, the tissue engagement member includes a disc-shaped member which extends radially outwardly of the tissue tensioner device shaft. The disc-shaped member can include a proximally located concavity and/or one or more ridges or teeth configured to engage tissue. In another embodiment, the tissue engagement member includes one or more fingers which extend radially outwardly of the tissue tensioner device shaft and proximally towards the shell assembly. In one embodiment, four curved fingers may be provided. In another embodiment, three or more substantially L-shaped fingers may be provided. Alternately, other tissue engagement member configurations may be used.

BRIEF DESCRIPTION OF THE DRAWINGS

Various embodiments of the presently disclosed surgical stapling device with tissue tensioner are disclosed herein with reference to the drawings, wherein:

FIG. 4 is a side cross-sectional view of the central body portion and distal head portion of the surgical stapling device shown in FIG. 1;

FIG. 5 is an enlarged view of the indicated area of detail shown in FIG. 4 with the tissue tensioning device in its advanced position;

FIG. 6 is a side cross-sectional view of the area of detail shown in FIG. 5 with the tissue tensioning device in a partially retracted position;

FIG. 7 is a side cross-sectional view of the central body portion and distal head portion of the surgical stapling device shown in FIG. 1 with the tissue tensioning device in a partially retracted position;

FIG. 8 is a side perspective view from the proximal end of the tissue tensioning device of the surgical stapling device shown in FIG. 1;

FIG. 8a is a side perspective view of the distal end of another embodiment of the tissue tensioning device shown in FIG. 8;

FIG. 9 is a side perspective view of the distal end of yet another embodiment of tissue tensioning device shown in FIG. 8;

FIG. 10 is a side perspective view of the distal end of yet another embodiment of the tissue tensioning device shown in FIG. 8;

FIG. 11 is a side perspective view of the distal end of yet another embodiment of the tissue tensioning device shown in FIG. 8;

FIG. 14 is a side perspective view of the distal end of the surgical stapling device shown in FIG. 1 positioned adjacent an access port to the anus with a purse-string suture applied to the internal hemorrhoids and/or mucosal tissue, the anvil in its unapproximated position, and the tissue tensioning device in its advanced position;

FIG. 15 is a side perspective view of the distal end of the surgical stapling device shown in FIG. 1 positioned through the access port beyond the internal hemorrhoids with the purse-string suture cinched about the tissue tensioner shaft, the anvil in its unapproximated position and the tissue tensioning device in its advanced position;

FIG. 16 is a side perspective view of the distal end of the surgical stapling device shown in FIG. 1 positioned through the access port beyond the internal hemorrhoids with the purse-string suture cinched about the tissue tensioner shaft, the anvil in its unapproximated position and the tissue tensioning device in a partially retracted position; and FIG. 17 is a side perspective view of the distal end of the surgical stapling device shown in FIG. 1 positioned through the access port beyond the internal hemorrhoids with the purse-string suture cinched about the tissue tensioner shaft, the anvil in its approximated position and the tissue tensioning device in its retracted position.

DETAILED DESCRIPTION OF THE EMBODIMENTS

Figure 1:
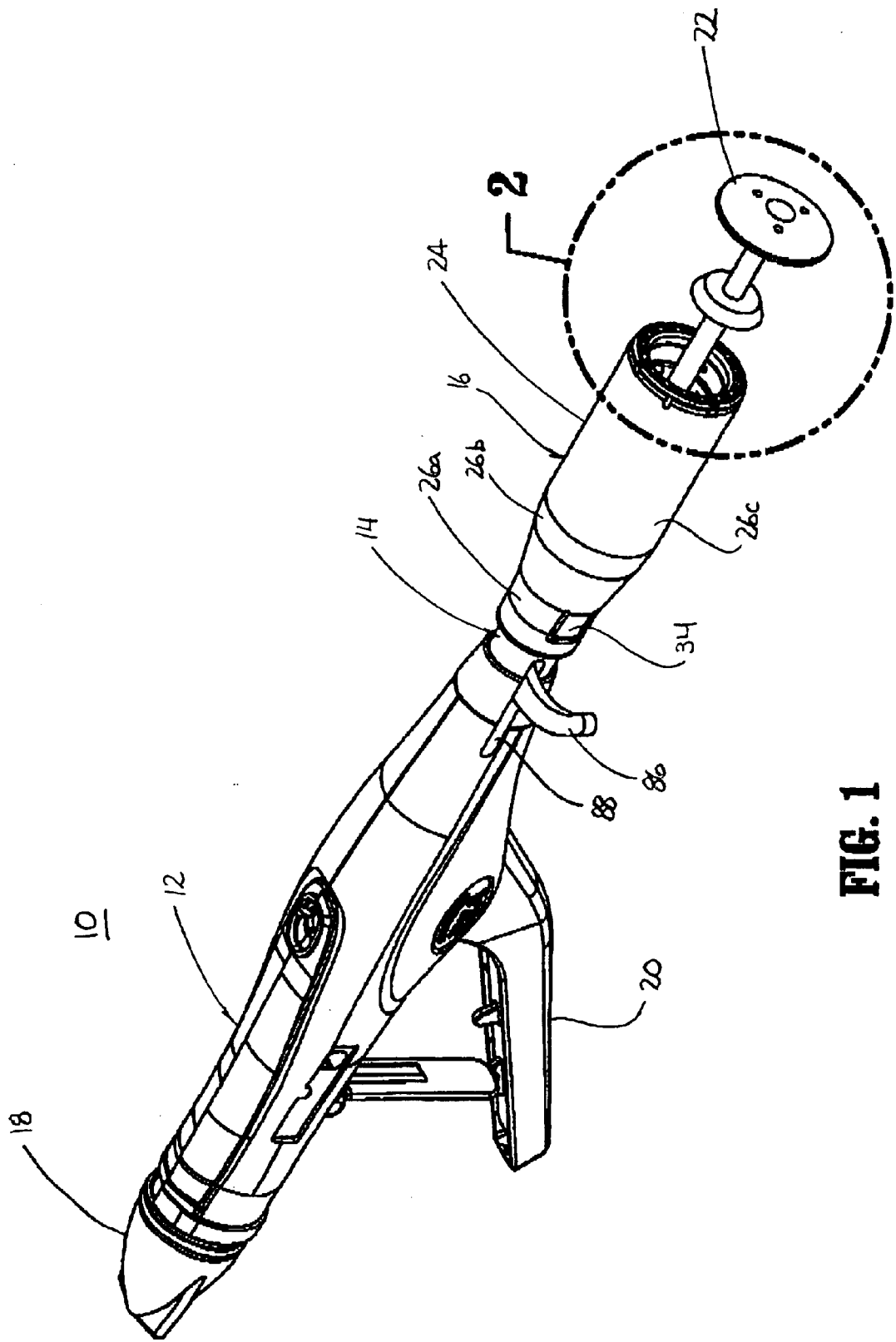
FIG. 1 is a side perspective view from the top of one embodiment of the presently disclosed surgical stapling device with the anvil in the unapproximated position.
Figure 2:
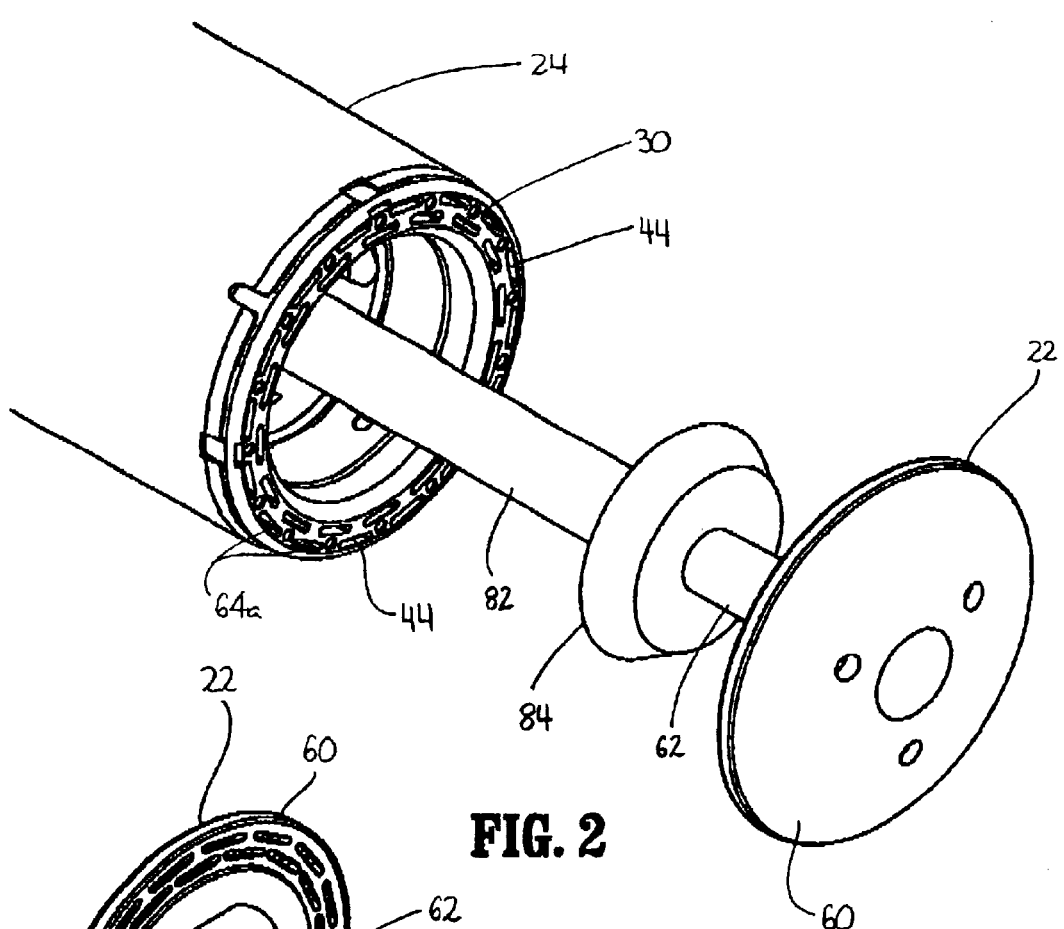
FIG. 2 is an enlarged view of the indicated area of detail shown in FIG. 1.
Figure 3:
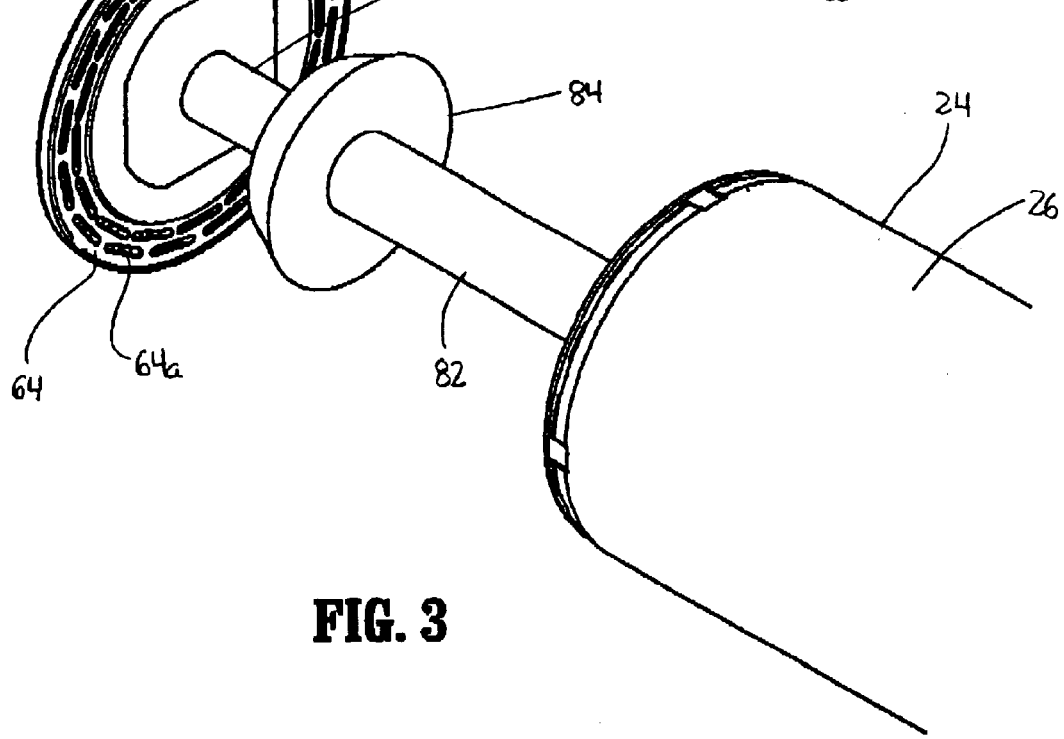
FIG. 3 is a side perspective view from the proximal end of the area of detail shown in FIG. 2.

Embodiments of the presently disclosed surgical stapling device will now be described in detail with reference to the drawings in which like reference numerals designate identical or corresponding elements in each of the several views. Throughout this description, the term "proximal" will refer to the portion of the device closest to the operator and the term "distal" will refer to the portion of the device furthest from the operator. U.S. provisional application Ser. No. 60/480,074 ("'074 application"), entitled Surgical Stapling Device, filed Jun. 20, 2003, under Express Mail #EV328280895US is incorporated herein in its entirety by reference.

FIGS. 1–8 illustrate one embodiment of the presently disclosed surgical stapling device shown generally as 10. Referring to FIG. 1, surgical stapling device 10 includes a proximal handle assembly 12, a central body portion 14 and a distal head portion 16. Proximal handle assembly 12 is substantially identical to the handle assembly described in the '074 application and will only be discussed briefly herein. Proximal handle assembly 12 includes a rotatable approximation knob 18 and a firing trigger 20. Approximation knob 18 is operable to move anvil 22 in relation to shell assembly 24 of head portion 16 between spaced and approximated positions and firing trigger 20 is operable to eject fasteners from shell assembly 24 and advance a knife blade through shell assembly 24 to cut tissue. Operation of rotatable knob 18 and firing trigger 20 are described in detail in the '074 application and will not be discussed in further detail herein.

Referring to FIGS. 2–7, head portion 16 includes anvil 22 and shell assembly 24. Except as otherwise noted, the components of stapling device 10 are formed from thermoplastics, e.g., polycarbonates, and metals, e.g., stainless steel and aluminum. The particular material selected to form a particular component of stapling device 10 will depend upon the strength requirements of the component. For example, the anvil may be formed from a metal, such as stainless steel and the housing of handle assembly 12 may be formed from plastic, such as polycarbonate. Alternately, materials not listed above having the requisite strength characteristics may be used to form the components of stapling device 10 provided the materials are suitable for surgical use.

Shell assembly 24 includes an outer housing or shell 26, a pusher back 28, a staple guide 30 and a cylindrical knife 32. Outer housing 26 of shell assembly 24 defines a throughbore and includes a reduced diameter proximal portion 26a, a diverging intermediate portion 26b and a cylindrical larger diameter distal portion 26c. Proximal portion 26a includes a pair of resilient fingers 34 (FIG. 1) configured to releasably engage engagement structure 36 formed on the distal end of central body portion 14. Pusher back 28 is slidably positioned within the throughbore of outer housing 26 and has a shape which corresponds to the shape of the throughbore. Because of the shape of outer housing 26 and pusher back 28, pusher back 28 will only slide distally within the outer housing 26 from its position shown in FIG. 4. The proximal end of pusher back 28 is operatively associated with a pusher 40 (FIG. 4) which is driven by firing trigger 20 in a manner described in detail in the '074 application. As shown in FIG. 4, the distal end of pusher back 28 includes a multiplicity of distally extending fingers 42 dimensioned to be slidably received within slots 44 formed in staple guide 30. Alternately, fingers 42 may be formed on a ring which is separate from pusher back 28. Slots 44 of staple guide 30 are dimensioned to receive staples 46 (FIG. 5) such that when pusher 40 is advanced via actuation of firing trigger 20, pusher back 28 is moved distally to move fingers 42 through slots 44 to eject staples 46 from staple guide 30. Staple guide 30 is secured in distal portion 26c of outer housing 26 of shell assembly 24 in a known manner, e.g., friction, adhesives crimping, etc.

An annular knife blade 50 is secured within a bore 52 defined within pusher back 28 and shell assembly housing 26 such as by press-fitting. Alternately, other techniques may be used to secure knife blade 50 within pusher back 28. Knife blade 50 includes an annular cutting edge 50a and is advanced with pusher back 28 when firing trigger 20 is actuated to dissect tissue.

Anvil 22 includes an anvil head 60 and an anvil shaft 62. Anvil head 60 includes an anvil plate 64 which includes a plurality of staple deforming pockets 64a (FIGS. 2 and 3) for receiving and deforming staples 46 ejected from staple guide 30. Anvil shaft 62 has a distal end connected to anvil head 60 and a proximal end operatively connected (not shown) to the approximation mechanism of stapling device 10 in a manner such as disclosed in the '074 application. When approximation knob 18 (FIG. 1) is rotated or actuated, anvil shaft 62 is retracted into or advanced from shell assembly 24. Although anvil head 60 and anvil shaft 62 are illustrated as being of monolithic construction, they may be formed separately and secured together. In one embodiment, anvil 22 is fixedly secured to the stapling device 10. Alternately, stapling device 10 may be adapted to receive a removable anvil and/or an anvil having a tiltable anvil head such as disclosed in the '074 application.

Referring to FIGS. 4–8, stapling device 10 includes a tissue tensioning device 80 supported by anvil shaft 62. In one embodiment, tissue tensioning device 80 includes a hollow shaft 82 having a radially extending tissue engagement member 84 formed at a distal end thereof and a tensioner trigger 86 formed at a proximal end thereof. Tensioner trigger 86 extends through an elongated slot 88 formed in the distal end of handle assembly 12 and central body portion 14. It is envisioned that trigger 86 may be positioned to extend through handle assembly 12 at a location adjacent firing trigger 20 to facilitate operation of firing trigger 20 and trigger 86 using a single hand. Elongated slot 88 should be of a length to permit engagement member 84 to be moved proximally in relation to anvil head 60 to adjust the depth of the internal hemorrhoids in relation to bore 52 of shell assembly 24 and to allow for approximation of anvil 22 and shell assembly 24. Although trigger 86 is illustrated as including a radially extending arm, other configurations are envisioned. For example, tensioner trigger 86 may be in the form of a slidable button, an annular or semi-annular collar, a T-bar, etc.

Referring also to FIG. 8, hollow shaft 82 of tissue tensioning device 80 defines a longitudinal bore 90 dimensioned to slidably receive anvil shaft 62. An indexing mechanism can be provided for controlling movement of hollow shaft 82 about anvil shaft 62. In one embodiment (FIGS. 5 and 6), the indexing mechanism includes a nub or projection 92 formed on anvil shaft 62 and a series of indentations 94 formed on an inner wall of hollow shaft 82. Engagement between nub 92 and one of indentations 94 releasably retains hollow shaft 82 at a fixed position in relation to anvil shaft 62. See FIG. 5. By applying a predetermined force to trigger 86, nub 92 can be disengaged from the indentation 94 and moved in relation to anvil shaft 62 into engagement with another indentation 94. See FIGS. 6 and 7. Relative movement between anvil shaft 62 and hollow shaft 82 is limited by engagement of trigger 86 with the proximal and distal ends of slot 88. It is envisioned that other means may be provided to limit movement of hollow shaft 82 about anvil shaft 62 (until a predetermined force is applied to trigger 86), e.g., frictional engagement between shaft 82 and shaft 62, a ratcheting mechanism, frictional engagement of tensioner trigger 86 within slot 88, etc.

Radially extending engagement member 84 of tissue tensioning device 80 is configured to engage tissue positioned between anvil head 60 and shell assembly 24 when tensioner trigger 86 is moved from an advanced position (FIG. 4) to a retracted position (FIG. 7) to move engagement member 84 from an advanced position (FIG. 4) to a retracted position (FIG. 7). Although engagement member 84 is illustrated as being disc-shaped in FIGS. 1–8, other configurations are envisioned. For example, the engagement member may include 1) a disc-shaped member 100 having a proximal concavity 102 (FIG. 8a); 2) a disc-shaped member 104 having a series of ridges or teeth 106 formed about an annular proximal edge thereof (FIG. 9); or 3) a series of curved fingers 108 and 108a (FIGS. 10 and 11). Fingers 108 curve radially outwardly from shaft 82 and extend proximally toward shell assembly 24. Fingers 108a are substantially L-shaped and have a distal end 108c which extend in a direction towards shell assembly 24. Although three fingers 108a and four fingers 108 are shown, it is envisioned that one or more fingers may be provided. Alternately, other configurations not shown here and capable of engaging tissue and/or a purse string suture may also be used.

Figure 12:
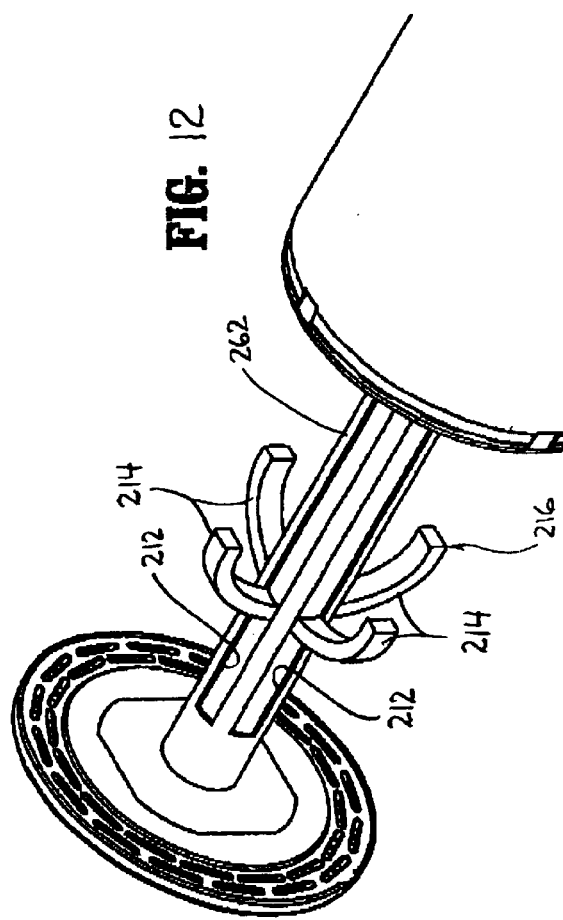
FIG. 12 is a side perspective view from the proximal end of the distal head portion of the surgical stapling device shown in FIG. 1 with the anvil in its unapproximated position and the tissue tensioning device in its partially retracted position.
Figure 13:
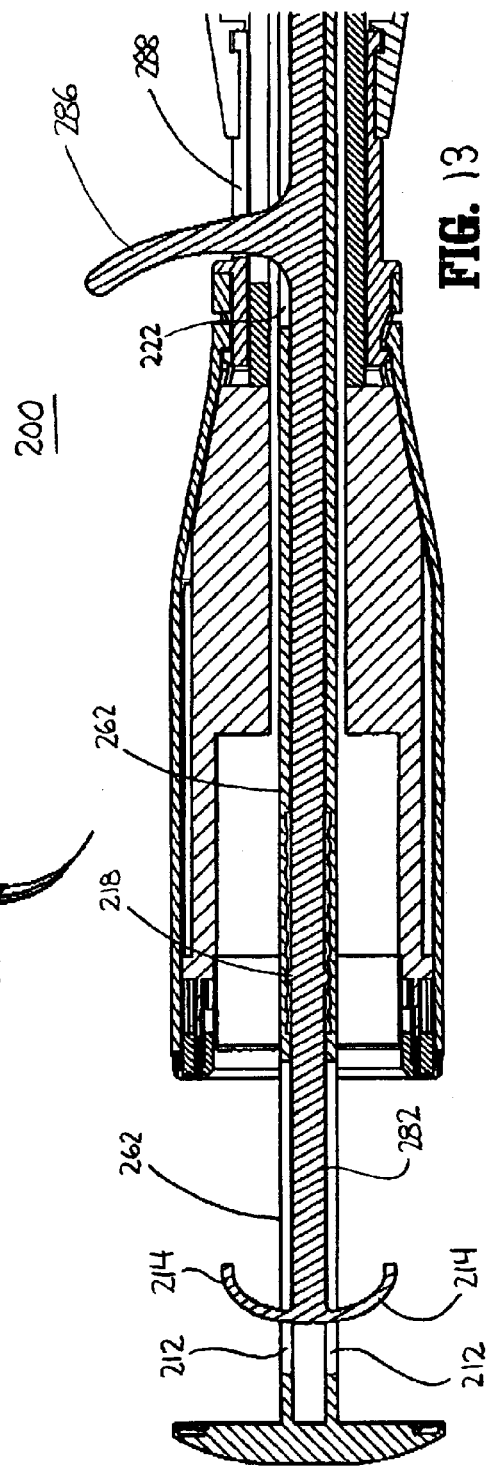
FIG. 13 is a side cross-sectional view of the central body portion and distal head portion of the surgical stapling device shown in FIG. 1 with the anvil in its unapproximated position and the tissue tensioning device in its partially retracted position.

FIGS. 12 and 13 illustrate another embodiment of the presently disclosed surgical stapling device shown generally as 200. Stapling device 200 includes a tissue tensioning device 210 having a tensioner shaft 282 which is slidably positioned within a longitudinal bore defined in anvil shaft 262. Elongated slots 212 are provided in a distal portion of anvil shaft 262 to facilitate passage of fingers 214 of the engagement member 216. It is envisioned that tissue engagement member 216 may be configured as shown in any of FIGS. 8–11 or assume other configurations capable of achieving the desired result. An indexing mechanism including a nub 218 formed on tensioner shaft 282 and a series of indentations 294 formed on an inner wall of anvil shaft 262 is also provided to limit movement of tensioning device 210 in relation to anvil shaft 262 until a predetermined force has been applied to trigger 286 of tensioning device 200. An elongated slot 222 is provided in a proximal portion of anvil shaft 262 and another elongated slot 288 is provided in central body portion 14 and handle assembly 12 to facilitate passage of trigger 286 from within anvil shaft 262 to a position to be engaged by an operator or surgeon. Tissue tensioning device 200 functions identically to tensioning device 80. Accordingly, the method of use of the tensioning device will be discussed only with reference to tensioning device 80.

Referring to FIGS. 14–17, the surgical stapling devices 10 and 200 are particularly suitable for use in surgical procedures for treating internal hemorrhoids from a patient. Such treatment may include partial removal of internal hemorrhoid(s) and/or mucosal tissue. During such a procedure, an access port 300 can be inserted into the anus to facilitate access to the internal hemorrhoids. Next, a purse string suture 302 is placed into, above or in the vicinity of each of the internal hemorrhoids 304 above the dentate line and the distal end of the surgical stapling device 10 is inserted through access port 300 into the anus and rectum. The tissue tensioner device 80 should be in the advanced position (FIG. 4) when the stapling device is inserted into the anus and rectum. In one embodiment, the purse string suture is placed about the entire circumference of the anus/rectum even though the hemorrhoids may not extend about the entire circumference of the anus/rectum. The anvil 22 and tissue tensioner device 80 are inserted past internal hemorrhoids 304 and through purse string suture 302. Thereafter, purse string suture 302 is cinched about tissue tensioner shaft 82 to draw internal hemorrhoids and/or mucosal tissue 304 towards and about anvil shaft 62 (FIG. 15). Next, tensioner trigger 86 (FIG. 1) is retracted to retract tissue engagement member 84 in relation to anvil shaft 62 and shell assembly 24. Tissue engagement member 84 is positioned and configured to engage internal hemorrhoids and/or mucosal tissue 304 and/or purse string suture 302 to adjust the depth of the internal hemorrhoids and/or mucosal tissue within bore 52 of shell assembly 24. When internal hemorrhoids 304 are positioned at the desired depth within shell assembly 24, the anvil 22 and shell assembly 24 are approximated by rotating approximation knob 18 in a manner described in the '074 application (FIG. 1). As anvil shaft 62 is drawn into shell assembly 24, tissue tensioning device 80 including engagement member 84 is drawn into shell assembly 24 to pull internal hemorrhoids and/or mucosal tissue 304 into the bore 52 defined by pusher back 28 and shell assembly 24 (FIG. 17). It is noted that tensioner device 80 may be repositioned during approximation of anvil 22 and shell assembly 24 by retracting or advancing tensioner trigger 86 to readjust the depth of internal hemorrhoids 304 within bore 52 of shell assembly 24.

When surgical stapling device 10 is fully approximated, firing trigger 20 can be actuated in a manner described in the '074 application to staple, sever and allow removal of internal hemorroids and/or mucosal tissue 304. Thereafter, stapling device 10 is removed from the anus with the excised internal hemorrhoids contained within bore 52 of pusher back 28 within shell assembly 24.

It is envisioned that instrument accessories may be used to assist in performing particular steps of the above described procedures. For example, a speculum may be inserted into the anus to simplify placement of the purse string suture by providing easier access to the surgical site. An obturator may also be used to assist in placement of the dialator. Further, an expandable introducer may be provided to reduce the trauma that results from insertion of the stapling device into the anus.

It will be understood that various modifications may be made to the embodiments disclosed herein. For example, the particular configuration of the tissue tensioning device may be changed to provide a more ergonomic or accessible trigger. Further, the tissue tensioning device shaft need not be rigid but may be formed of a resilient or bendable wire or rod having a tissue engaging segment. Moreover, the position of the tensioner trigger on the device may be changed, i.e., moved to the handle assembly, to simplify operation of the tensioning device or to facilitate operation of the firing trigger and tensioner trigger using a single hand. Therefore, the above description should not be construed as limiting, but merely as exemplifications of preferred embodiments. Those skilled in the art will envision other modifications within the scope and spirit of the claims appended hereto.

What is claimed is:

1. A surgical stapling device comprising:
   a body portion;
   a head portion supported on the distal end of the body portion, the head portion including an anvil and a shell assembly, the anvil being movable in relation to the shell assembly between approximated and unapproximated positions; and
   a tissue tensioning device including a tissue engagement member, the tissue engagement member being positioned between the anvil and the shell assembly and movable in relation to the anvil and in relation to the shell assembly.

2. A surgical stapling device according to claim 1, wherein the anvil includes an anvil head and an anvil shaft and the tissue tensioning device is movably supported by the anvil shaft.

3. A surgical stapling device according to claim 2, wherein the tissue tensioning device includes a hollow shaft which is slidably positioned about the anvil shaft.

4. A surgical stapling device according to claim 3, wherein the tissue engagement member extends radially outwardly from the hollow shaft.

5. A surgical stapling device according to claim 4, wherein the tissue engagement member includes a disc-shaped member positioned about the hollow shaft.

6. A surgical stapling device according to claim 5, wherein the disc-shaped member has a diameter which is smaller than a diameter of the anvil head.

7. A surgical stapling device according to claim 6, wherein the disc-member includes a proximal concavity.

8. A surgical stapling device according to claim 5, wherein the disc-shaped member includes a proximal concavity.

9. A surgical stapling device according to claim 4, wherein the tissue engagement member includes at least one finger.

10. A surgical stapling device according to claim 9, wherein the at least one finger is curved and extends radially outwardly and towards the shell assembly.

11. A surgical stapling device according to claim 10, wherein the at least one finger includes four fingers.

12. A surgical stapling device according to claim 9, wherein the at least one finger is substantially L-shaped and extends radially outward of the hollow shaft and towards the shell assembly.

13. A surgical stapling device according to claim 12, wherein the at least one finger includes three fingers.

14. A surgical stapling device according to claim 3, wherein the tissue tensioning device further includes a trigger which extends through an elongated slot formed in the surgical stapling device.

15. A surgical stapling device according to claim 14, wherein the elongated slot is formed at least partially through the central body portion.

16. A surgical stapling device according to claim 2, wherein the shell assembly defines a bore, the tissue engagement member being positioned at least partially within the bore when the anvil is in the approximated position.

17. A surgical stapling device according to claim 2, wherein the tissue tensioning device includes a solid shaft, the solid shaft being slidably positioned within a longitudinal bore formed in the anvil shaft.

18. A surgical stapling device according to claim 17, wherein an internal wall of the longitudinal bore includes a series of longitudinally arranged indentations and the solid shaft of the tissue tensioning device includes an outwardly extending nub, the nub being selectively movable into engagement with any one of the indentations to selectively retain the tissue tensioner device at a fixed positions in relation to the anvil shaft.

* * * * *